US011004565B2

(12) United States Patent
Abramoff

(10) Patent No.: US 11,004,565 B2
(45) Date of Patent: May 11, 2021

(54) DATA AGGREGATION, INTEGRATION AND ANALYSIS SYSTEM AND RELATED DEVICES AND METHODS

(71) Applicant: Digital Diagnostics Inc., Coralville, IA (US)

(72) Inventor: Michael D. Abramoff, University Heights, IA (US)

(73) Assignee: Digital Diagnostics Inc., Coralville, IA (US)

( * ) Notice: Subject to any disclaimer, the term of this patent is extended or adjusted under 35 U.S.C. 154(b) by 85 days.

(21) Appl. No.: 16/362,174

(22) Filed: Mar. 22, 2019

(65) Prior Publication Data

US 2019/0295722 A1 Sep. 26, 2019

Related U.S. Application Data

(60) Provisional application No. 62/646,730, filed on Mar. 22, 2018.

(51) Int. Cl.
| | |
|---|---|
| *G06K 9/62* | (2006.01) |
| *G16H 50/20* | (2018.01) |
| *G06F 16/23* | (2019.01) |
| *G06N 3/08* | (2006.01) |
| *G16H 30/40* | (2018.01) |
| *G16H 50/70* | (2018.01) |
| *G06K 9/66* | (2006.01) |

(52) U.S. Cl.
CPC ......... *G16H 50/20* (2018.01); *G06F 16/2379* (2019.01); *G06K 9/6256* (2013.01); *G06N 3/084* (2013.01); *G16H 30/40* (2018.01); *G16H 50/70* (2018.01); *G06K 9/66* (2013.01)

(58) Field of Classification Search
CPC ........ G16H 50/20; G16H 30/40; G16H 50/70; G16H 40/67; G16H 30/20; G06F 16/2379; G06N 3/084; G06N 20/20; G06N 20/10; G06K 9/6256; G06K 9/66; G06K 2209/05; G06K 9/6277
USPC .......................................... 382/157
See application file for complete search history.

(56) References Cited

U.S. PATENT DOCUMENTS

| | | | |
|---|---|---|---|
| 10,002,322 B1 * | 6/2018 | Ravindran | G06Q 10/04 |
| 2019/0043201 A1 * | 2/2019 | Strong | G06K 9/00624 |

OTHER PUBLICATIONS

Powles, J. et al., "Google DeepMind and healthcare in an age of algorithms," Health and Technology, Dec. 2017, pp. 351-367, vol. 7, No. 4.

* cited by examiner

*Primary Examiner* — Charlotte M Baker
(74) *Attorney, Agent, or Firm* — Fenwick & West LLP

(57) ABSTRACT

A system for recording, storing and processing diagnostic information, including: a computer implementing a computer-readable media including digital data and ground truth; a registry constructed and arranged to store and associate transactions or accesses on the data; and a machine learning system that considers each learning step modification a microtransaction for the data used in that step and which is recorded in the transaction registry. Other embodiments of this aspect include corresponding computer systems, apparatus, and computer programs recorded on one or more computer storage devices, each configured to perform the actions of the methods.

21 Claims, 3 Drawing Sheets

DATA AGGREGATION, INTEGRATION AND ANALYSIS SYSTEM AND RELATED DEVICES AND METHODS

CROSS-REFERENCE TO RELATED APPLICATION(S)

This application claims priority to U.S. Provisional Application No. 62/646,730 filed Mar. 22, 2018 and entitled "DATA AGGREGATION, INTEGRATION AND ANALYSIS SYSTEM AND RELATED DEVICES AND METHODS," which is hereby incorporated by reference in its entirety under 35 U.S.C. § 119(e).

TECHNICAL FIELD

The disclosed technology relates generally to the collection, storage and aggregation of information and in particular, to the devices, methods, and design principles allowing for the use of digital data to enhance medical diagnostics.

BACKGROUND

Diagnostic AI is of enormous importance for increasing health care productivity, and improving the accessibility, quality and efficiency of medical diagnostics. Image based diagnostics are the most attractive because objective sensor data is a huge advantage over provider obtained and recorded data for example from the history of present illness as the communication by both patient and provider add additional noise on top of the already noise underlying clinically relevant data.

A major limitation of diagnostic AI, and especially diagnostic AI based on images is that a large amount of training data is needed, and unlike computer vision and autonomous vehicle AI applications, medical data is scarce, because of ethical considerations, obtaining it can harm the patient through radiation, allergic reactions to contrast agents, and the like, and is also scarce because of the enormous resources for clinical expertise required to obtain and evaluate the data, such as biopsies and expert readings to create ground truth.

Thus, for entities interested in creating diagnostic AI, getting access to patient image data is crucial. However, many hospitals and other providers and even patients have image data, but are reluctant to share or sell it to AI companies, because of uncertainty about how the images will be used. For example, Google Deepmind an AI diagnostics company, obtained image data from an NHS hospital in London without adequate protections and was criticized and punished for that. See, e.g. Powles et al, Google DeepMind and Healthcare in an Age of Algorithms, 7 HEALTH TECHOL. 4, 351-367 (2017).

Therefore, there is a need in the art for the technology and design principles allowing for tracking and authenticating and attributing patient data, such as imaging data, for use in artificial intelligence systems. Specifically, patients and providers and other entities desire a) transparency and tracking how 'their' data is used exactly, and b) attribution of their data contribution to the return from the AI diagnostic system (for example, from the $1 B the AI made last year, how much of that can be attributed to my image).

BRIEF SUMMARY

Disclosed herein are several devices, systems and methods relating to the collection, storage, disassociation, re-association and verification of data, particularly data related to medical diagnostic examinations.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. Other embodiments of this aspect include corresponding computer systems, apparatus, and computer programs recorded on one or more computer storage devices, each configured to perform the actions of the methods. One general aspect includes a system for recording, storing and processing diagnostic information, including: a computer implementing a computer-readable media including digital data and ground truth; a registry constructed and arranged to store and associate transactions or accesses on the data; and a machine learning system that considers each learning step modification a microtransaction for the data used in that step and which is recorded in the transaction registry. Other embodiments of this aspect include corresponding computer systems, apparatus, and computer programs recorded on one or more computer storage devices, each configured to perform the actions of the methods.

Implementations may include one or more of the following features. The system where the digital data is imagining data. The system further including an imagining device. The system where the blockchain is a public registry. The system where the blockchain is a private registry or a restricted access registry. The system where the machine learning algorithm is configured to be trained by backpropagation. The system where performance of the machine learning algorithm is assessed with each micro transaction and any change in performance are attributed on the ledger to the data element responsible for the change. The system where change in performance is measured by test data AUC, sensitivity, or specificity, or other aggregate metrics. The system where the machine learning algorithm includes an n-layer neural network. Implementations of the described techniques may include hardware, a method or process, or computer software on a computer-accessible medium.

One general aspect includes a method for attribution of data to an algorithm including: registering a pool of images on a ledger, attributing each image of the pool of images with an image-specific truth data set on the ledger, training a machine learning algorithm to one or more of the images and registering the training of the machine learning algorithm a plurality of parameters to the one or more images on the ledger, registering each modification made to the machine learning algorithm on the ledger and attributing its modification to image that resulted in the modification, and assessing performance of the machine learning algorithm with each modification on a test data set and attributing any change to the image that resulted in the change. Other embodiments of this aspect include corresponding computer systems, apparatus, and computer programs recorded on one or more computer storage devices, each configured to perform the actions of the methods.

Implementations may include one or more of the following features. The method where the machine learning algorithm is a n-layer neural network. The method further including back propagating the training of the machine learning algorithm. The method where assessing performance is measured by test data AUC, sensitivity, or specificity. The method where assessing performance is measured by test data AUC. The method where the ledger is a distributed registry. The method where the foregoing steps are repeated until a predetermined threshold of performance is reached. The method where the image-specific data for each image includes patient health data. The method where the patient health data is selected from a group including: genetic data, patient history data, electronic health record data, behavioral data, clinical outcome data, and/or life history data. The method where the image-specific data for each image includes image source data. The method where the image-specific data for each image includes image acquisition data. Implementations of the described techniques may include hardware, a method or process, or computer software on a computer-accessible medium.

In certain examples, every update of a parameter with a specific item of digital data constitutes a transaction for that parameter on the one hand and for that item of digital data, and this microtransaction is recorded in the distributed registry.

While multiple embodiments are disclosed, still other embodiments of the disclosure will become apparent to those skilled in the art. As will be realized, the disclosed apparatus, systems, and methods are capable of modifications in various aspects, all without departing from the spirit and scope of the disclosure. Accordingly, the drawings and detailed description are to be regarded as illustrative in nature and not restrictive.

DETAILED DESCRIPTION

Discussed herein are various embodiments relating to a storage and validation/identification system 10 used to tag or otherwise associate digital information, such as digital image information, with specific identifying information, such as patient information. The various implementations of the disclosed identification system improve upon the prior art by allowing for the aggregation of the identifying information for subsequent association with the digital information. Additionally, in alternate embodiments, the identification system may include a blockchain, further improving upon the art.

Described herein are various embodiments relating to systems and methods for improving the reliability and identification of digital data, such as on the basis of ground truth, i.e., via direct observation or recording, rather than inference. It is understood that various implementations relate to the use of machine learning and blockchain technologies to securely collect, aggregate and analyze digital data, such as digital image data.

It is understood that various implementations of the system described herein improving the aggregation and trackability of various forms of data. It is further understood that in various implementations, multiple types of data from several modalities can be collected and associated, for example digital data, such as imaging data; and ground truth, including reference standards, diagnostic, or biopsy data specific to an individual patient and disease.

It would be appreciated that in various implementations, other kinds of data are contemplated, certain non-limiting examples being genetic data, patient history data, electronic health record data, behavioral data, clinical outcome data, life history data, and in fact any data that can contribute to diagnostic accuracy of a diagnostic system. Other data forms would be appreciated by those of skill in the art.

In certain implementations, it is understood that at the digital information is collected in a clinical or medical setting, and the identification system disclosed herein uses a processing system to collect data, such as imaging data from a patient and device. Additional implementations are of course possible.

Although multiple embodiments, including various devices, systems, and methods are described herein as an "attribution system" or "identification system," this is in no way intended to be restrictive.

Figure 1:
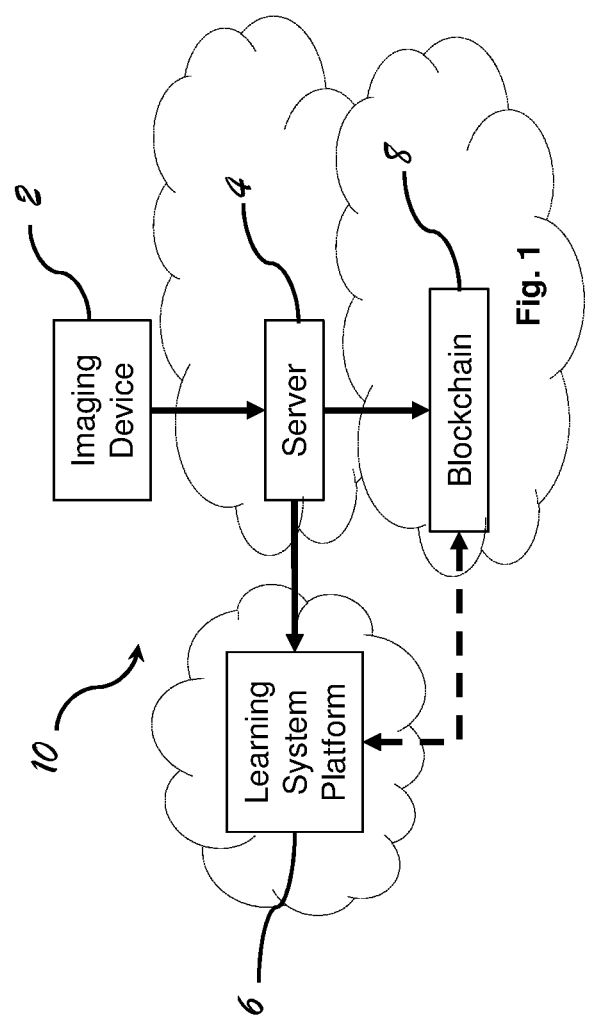
FIG. 1 is a schematic diagram of one implementation of the system.

Turning to the figures in greater detail, a brief schematic representation of one general implementation is shown in FIG. 1. In these implementations, the system 10 comprises several components constructed and arranged so as to record and transmit information, including such optional components as an imaging device 2, a server 4, a learning system platform 6 and a distributed registry such as a blockchain storage system 8. Various alternate implementations are of course possible, depending on the specific application.

It is understood that the server 6 may be optional in certain implementations, but that in implementations like that of FIG. 1 the various components are inter-connected via the internet or other electronic communication systems, such that the storage system 8 can be accessed by various researchers working separately or remotely and independently.

Figure 2:
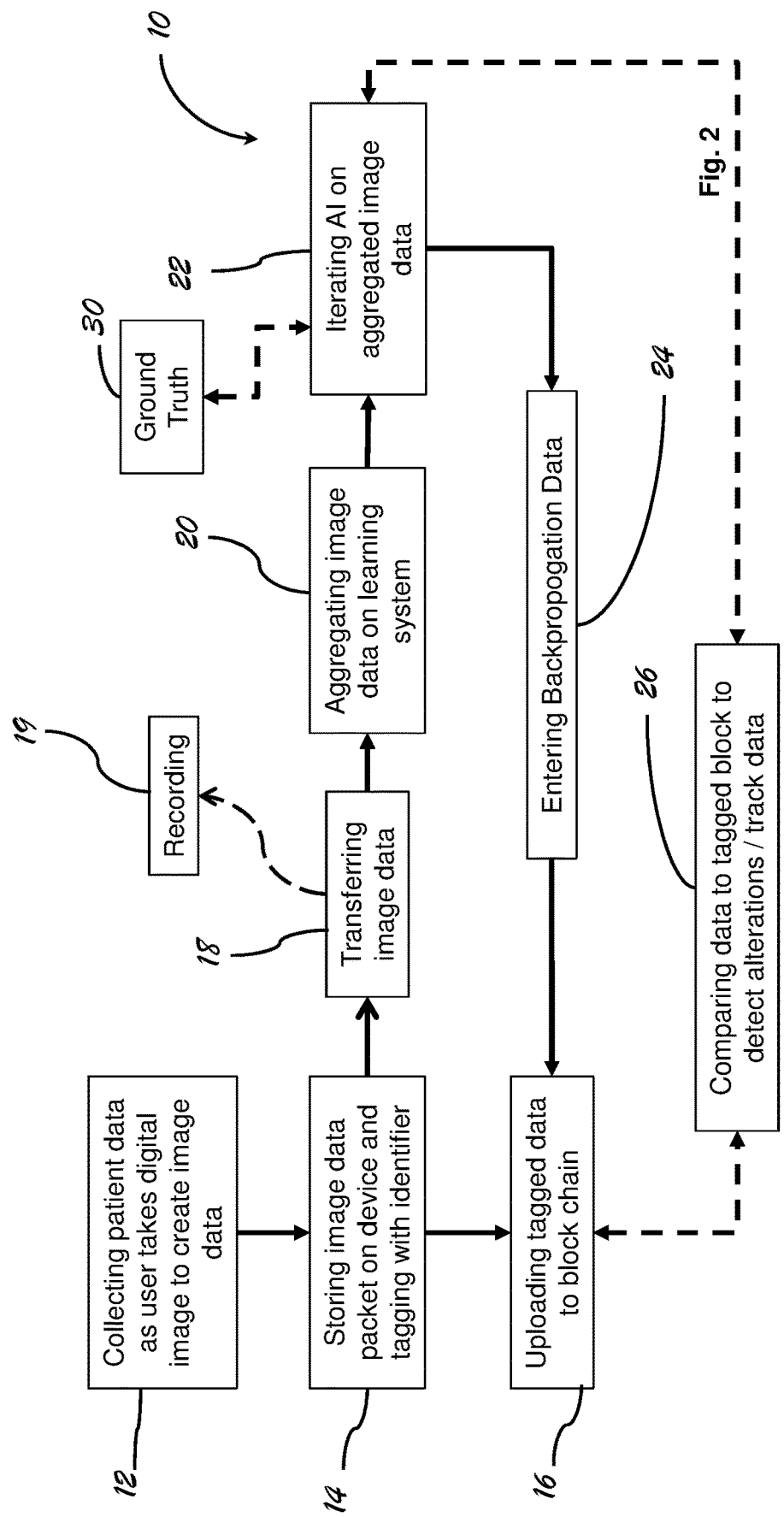
FIG. 2 is a further schematic diagram of an exemplary implementation of the system.

In use according to these implementations, and as shown in the implementation of FIG. 2, the system 10 is constructed and arranged to execute or otherwise perform one or more optional steps. It is understood that the optional steps can be performed in any order, and that in various implementations certain steps may be added or omitted. It is further understood that in certain implementations, a cycle of steps may be executed, and that in certain iterations various steps are added or omitted to the cycle.

In one such optional step shown in FIG. 2, the system collects digital data via a collection step (box 12). The type and amount of digital data collected and stored can vary among various embodiments. In various implementations, certain non-limiting examples of this collected digital data include digital image data, image acquisition parameters, data related to the institution acquire the digital image, and the like.

In an optional tagging and storing step (box 14), the system 10 is constructed and arranged to tag, process and store collected digital data to create a digital file or packet, such as via a workstation and any of the incorporated imaging devices configured to record and execute computer-executable media. This locally-stored and tagged data can be compared with copies of the digital data, as described below in relation to the comparing step (box 26).

In various implementations of the tagging and storing step (box 14), the data is tagged as follows.

In an uploading step (box 16), the tagged digital data is assigned, through the distributed registry, an individual block to uniquely identify it, and those blocks are recorded in the public or private distributed transaction ledger to start the chain for that block. This uploading or assigning and recording step can be executed via any of the understood methods of recording data on a blockchain, and would be readily appreciated by those of skill in the art. It is further appreciated that the recorded data may be aggregated for use, as discussed below.

In alternate embodiments, the tagged data can be stored locally, on a database, or other system for storage as recognized by the art. After storage, the packet can be compared to data from subsequent steps for authentication and re-association of various portions of the data, for example, an individual researcher's contribution to the algorithm, as would be appreciated by one of skill in the art.

Continuing with the implementations of FIG. 2, after collection, the stored digital data may be transferred (box 18) in a further optional step through various research and storage facilities, where it can be used for research and analysis.

In certain implementations, each time there is a transfer or access of the data—uniquely identified by the block—this transfer or accessing may be recorded in the distributed transaction ledger of the blockchain or other storage medium in an optional transfer recording step (box 19).

Staying with the transferred data of FIG. 2, the transferred data can in turn be aggregated with other such data from a variety of researchers, institutions or studies via an optional aggregation step (box 20), such as on a database or other storage medium.

As would be fully appreciated by one of skill in the art, in certain implementations a learning system (shown in box 20 in FIG. 2 and at 6 in FIG. 1) can implement a learning step such as an algorithm or machine learning protocol from the aggregated digital data from a plurality of subjects, for performing diagnostic or other clinical tasks after implementation is complete, such as by utilizing ground truth (box 30).

In these various implementations, the aggregated digital data for which all transactions so far have been recorded in the distributed ledger can be accessed and associated, such that the algorithm or other machine learning protocol parameters, thresholds and/or steps can be updated through various iterations on the basis of an error function using an element of the stored and/or associated digital data.

That is, in certain implementations, and as depicted in FIG. 2, the digital data can be iterated upon in an optional iteration step (box 22), such as via a machine learning algorithm. In various implementations, the machine learning algorithm is an n-layer neural network.

According to exemplary implementations, the machine learning algorithm (shown in FIGS. 2 and 3 at box 22) is trained on a set of digital data such as images with a unique block, which have been previously associated with a plurality of diagnoses, ground truths (box 30) or reference standards, with all these associations recorded in the distributed ledger, with a unique block ground truth.

As the machine learning algorithm (box 22) is trained, each incremental modification of the weights or other parameters algorithm attributable to a specific block—such as an image with associated reference standards, ground truths and the like—is recorded as a microtransaction on the distributed ledger (shown in FIG. 1 at 8). Thus, when AI or machine learning training is finished, the contribution to each weight or parameter of a unique image (with ground truth) can be determined, as can the contribution to a specific increment in accuracy.

In certain aspects the updating of machine learning parameters is done through an optional backpropagation step (box 24). Every update of a parameter with a specific item of digital data (uniquely identified by its block) constitutes a (micro) transaction for that parameter on the one hand and for that item of digital data, and this microtransaction is recorded in the distributed registry (box 14, and also shown at box 8 in FIGS. 1 and 3).

It is understood that in various implementations, the disclosed system 10 can attribute the effect for each individual patient that provided an image, as well as the effect for each doctor that ordered the image, took the image, provided a reading or diagnosis other form of reference standard or ground truth (box 30).

Figure 3:
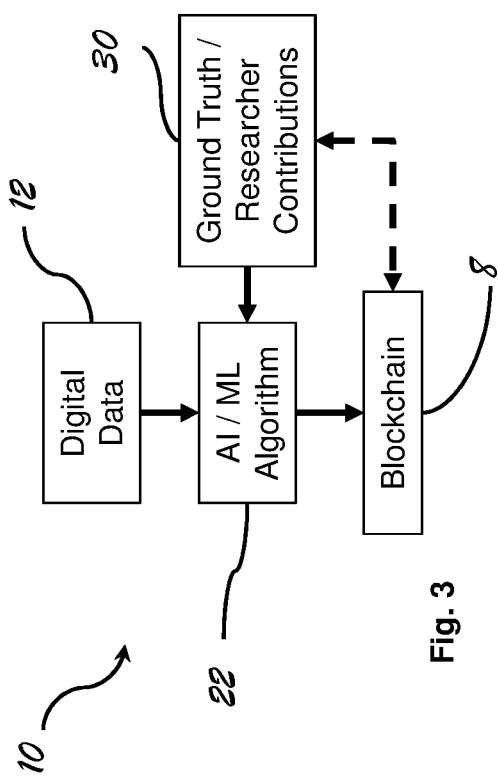
FIG. 3 depicts additional aspects of the schematics of FIGS. 1 and 2.

As a result, the relative contribution of individual images on machine learning algorithm performance can be attributed to specific images (and ground truths) and recorded in the ledger, as is shown at box 30 in FIG. 3. In certain implementations, machine learning algorithm performance is assessed based on test data set performance, as measured by Area under the curve ("AUC"), sensitivity, or specificity, or other metrics well-appreciated and understood in the art.

It is understood that in various implementations, this can be done via a distributed registry, such as a public registry or private or restricted access registry. It is understood that such use of a distributed registry provides numerous advantages to certain aspects of the system, including the prevention of fraud and corruption.

In various implementations, attribution of ground truth to digital data can be done prior to execution of the algorithm via a picture archival system (PACS). It is understood that in certain of these implementations, the attribution is used to determine and/or derive individual data elements from the ground truth block to associate with machine learning performance, such as a Convolutional Neural Network and end results.

Further, in additional implementations, the algorithmic performance is defined on a set of test data as AUC, sensitivity, or specificity. In yet further implementations, the attribution is used to determine to derive the individual data element contributions to machine learning output of a specific test data element, and to compensate individual researchers for those contributions.

To produce better algorithms and to further determine the importance of variables in the machine learning model, enhanced classification and regression tree approaches may be used. For example, classification & regression trees, random forest, boosted trees, support vector machines, neural networks may be used, as well as other machine learning techniques previously described and understood in the art.

The output may be in the form of a graph indicating the prediction or probability value along with related statistical indicators such as p-values, chi-scores and the like. In various implementations, these results can be re-introduced into the system 10 or elsewhere to continually improve the functions of the system, including by updating the various thresholds used throughout. It is understood that these implementations are also able to trend the respective data values and readings to improve the performance of the device, system and methods. In these implementations, for example, a continuous stream of trend data that can be used to provide additional optional evaluation steps, and trends over time can be identified. In various implementations, the model can provide additional program data to improve accuracy, as well as be included in aggregation.

Although the disclosure has been described with reference to certain embodiments, persons skilled in the art will recognize that changes may be made in form and detail without departing from the spirit and scope of the disclosed apparatus, systems and methods. Such that the various embodiments and steps described can be performed in a variety of orders and combinations without departing from the scope of the disclosure.

What is claimed is:

1. A non-transitory computer-readable medium comprising memory with instructions encoded thereon for attribution of data to an algorithm, the instructions, when executed, causing one or more processors to perform operations, the instructions comprising instructions to:
    (a) register a pool of images on a ledger;
    (b) attribute each image of the pool of images with an image-specific truth data set on the ledger;
    (c) train a machine learning algorithm to one or more of the images and registering the training of the machine learning algorithm a plurality of parameters to the one or more images on the ledger;
    (d) register each modification made to the machine learning algorithm on the ledger and attributing its modification to image that resulted in the modification; and
    (e) assess performance of the machine learning algorithm with each modification on a test data set and attributing any change to the image that resulted in the change.

2. The non-transitory computer-readable medium of claim 1, wherein the machine learning algorithm is a n-layer neural network.

3. The non-transitory computer-readable medium of claim 1, further comprising back propagating the training of the machine learning algorithm.

4. The non-transitory computer-readable medium of claim 1, wherein assessing performance is measured by test data AUC, sensitivity, or specificity.

5. The non-transitory computer-readable medium of claim 4, wherein assessing performance is measured by test data AUC.

6. The non-transitory computer-readable medium of claim 1, wherein the ledger is a distributed registry.

7. The non-transitory computer-readable medium of claim 1, wherein the steps (a)-(e) are repeated until a predetermined threshold of performance is reached.

8. The non-transitory computer-readable medium of claim 1, wherein the image-specific data for each image comprises patient health data.

9. The non-transitory computer-readable medium of claim 8, wherein the patient health data is selected from a group consisting of: genetic data, patient history data, electronic health record data, behavioral data, clinical outcome data, life history data.

10. The non-transitory computer-readable medium of claim 1, wherein the image-specific data for each image comprises image source data.

11. A method for attribution of data to an algorithm comprising:
    (a) registering a pool of images on a ledger;
    (b) attributing each image of the pool of images with an image-specific truth data set on the ledger;
    (c) training a machine learning algorithm to one or more of the images and registering the training of the machine learning algorithm a plurality of parameters to the one or more images on the ledger;
    (d) registering each modification made to the machine learning algorithm on the ledger and attributing its modification to image that resulted in the modification; and
    (e) assessing performance of the machine learning algorithm with each modification on a test data set and attributing any change to the image that resulted in the change.

12. The method of claim 11, further comprising back propagating the training of the machine learning algorithm.

13. The method of claim 11, wherein assessing performance is measured by test data AUC, sensitivity, or specificity.

14. The method of claim 13, wherein assessing performance is measured by test data AUC.

15. The method of claim 11, wherein the ledger is a distributed registry.

16. The method of claim 11, wherein the steps (a)-(e) are repeated until a predetermined threshold of performance is reached.

17. The method of claim 11, wherein the image-specific data for each image comprises patient health data.

18. The method of claim 17, wherein the patient health data is selected from a group consisting of: genetic data, patient history data, electronic health record data, behavioral data, clinical outcome data, life history data.

19. The method of claim 11, wherein the image-specific data for each image comprises image source data.

20. The method of claim 11, wherein the image-specific data for each image comprises image acquisition data.

21. The method of claim 11, wherein the machine learning algorithm is a n-layer neural network.

* * * * *